(12) United States Patent
Byun et al.

(10) Patent No.: US 10,562,879 B2
(45) Date of Patent: Feb. 18, 2020

(54) METHOD FOR PREPARING THIENYL ALANINE HAVING OPTICAL ACTIVITY

(71) Applicant: AMINOLOGICS CO., LTD., Seoul (KR)

(72) Inventors: Il-Suk Byun, Seongnam-si (KR); Jung-Ho Lee, Incheon (KR); Hyun-Seok Lee, Seongnam-si (KR); Won-Sup Kim, Seongnam-si (KR)

(73) Assignee: AMINOLOGICS CO., LTD., Seoul (KR)

( * ) Notice: Subject to any disclaimer, the term of this patent is extended or adjusted under 35 U.S.C. 154(b) by 0 days.

(21) Appl. No.: 15/762,370

(22) PCT Filed: Sep. 9, 2016

(86) PCT No.: PCT/KR2016/010193
§ 371 (c)(1),
(2) Date: Mar. 22, 2018

(87) PCT Pub. No.: WO2017/052122
PCT Pub. Date: Mar. 30, 2017

(65) Prior Publication Data
US 2018/0290996 A1    Oct. 11, 2018

(30) Foreign Application Priority Data
Sep. 25, 2015  (KR) .......... 10-2015-0136527

(51) Int. Cl.
*C07D 333/24* (2006.01)

(52) U.S. Cl.
CPC ........ *C07D 333/24* (2013.01); *C07B 2200/07* (2013.01)

(58) Field of Classification Search
CPC .................................................. C07D 333/24
USPC .................................................. 549/76
See application file for complete search history.

(56) References Cited

U.S. PATENT DOCUMENTS 5,688,672 A    11/1997 Kretzschmar et al.
2012/0041225 A1    2/2012 Vaidya

FOREIGN PATENT DOCUMENTS

| EP | 0 581 250 A2 | 7/1993 |
|---|---|---|
| JP | 61-501704 A | 8/1986 |
| KR | 10-2003-0020430 A | 3/2003 |

OTHER PUBLICATIONS

Kozma et al., Chirality (1999) vol. 11, pp. 373-375.*
Christian Döbler et al., "Unusual amino acids IV. Asymmetric synthesis of thienylalanines," Tetrahedron: Asymmetry, 1993.
Johannes Meiwes et al., "Asymmetric synthesis of l-thienylalanines," Tetrahedron: Asymmetry, 1997.
Csaba Paizs et al., "The Interaction of Heteroaryl-Acrylates and Alanines with Phenylalanine Ammonia-Lyase from Parsley," Chem. Eur. J., 2006.
Brad M. Cox et al., "Enhanced Conversion of Racemic r-Arylalanines to (R)-β-Arylalanines by Coupled Racemase/Aminomutase Catalysis," J. Org. Chem., 2009.
Dunn, F. W., "Preparation and microbiological properties of tripeptides of β-(2-thienyl)alanine," J. Biol. Chem., 1959.
Yamada, T. et al., "Separation of peptide diastereomers by reversed-phase highperformance liquid chromatography and its applications. IVa. New derivatization reagent for the enantiomeric analysis of α- and β-amino acids," Journal of Chromatography, 1990.
Myung Ho Hyun et al., "Preparation and application of a new ligand exchange chiral stationary phase for the liquid chromatographic resolution of a-amino acid enantiomers," Journal of Chromatography A, 2002.
International Search Report dated Dec. 19, 2016 in connection with PCT/KR2016/010193.
Search Report dated Jul. 23, 2018, in connection with European Patent Application No. 16848848.4.
Lipkowski, A.W. et al., (1980) "Resolution of [beta]-2-Thienylalanine Enantiomers by a Convenient Method," Polish Journal of Chemistry.
Pálovics, E. et al. (2012) "Separation of the Mixtures of Chiral Compounds by Crystallization," Advances in Crystallization Processes.

* cited by examiner

*Primary Examiner* — Taofiq A Solola
(74) *Attorney, Agent, or Firm* — John P. White; Cooper & Dunham LLP

(57) ABSTRACT

This invention relates to a method of preparing optically active β-2-thienyl-alanine, and more particularly to a method of preparing optically active β-2-thienyl-L-alanine or optically active β-2-thienyl-D-alanine through an optical resolution reaction using chiral dibenzoyl tartaric acid or a derivative thereof as an optical resolving agent.

6 Claims, 1 Drawing Sheet

METHOD FOR PREPARING THIENYL ALANINE HAVING OPTICAL ACTIVITY

CROSS-REFERENCE TO RELATED APPLICATIONS

This application is a § 317 national stage of PCT International Application No. PCT/KR2016/010193, filed Sep. 9, 2016, claiming priority of Korean Patent Application No. KR 10-2015-0136527, filed Sep. 25, 2015, the contents of each of which are hereby incorporated by reference into the application.

TECHNICAL FIELD

The present invention relates to a method of preparing optically active β-2-thienyl-alanine, and more particularly to a method of preparing a β-2-thienyl-alanine optical isomer having high optical purity from β-2-thienyl-DL-alanine using an optical resolving agent.

BACKGROUND ART

Isomers may have different properties depending on the steric configurations thereof, and the effects thereof may become significantly different if there is a pharmacological function. Hence, a chiral compound is typically used in a manner in which it is separated into pure isomer compounds, and thus it is necessary to develop a technique for separating a chiral compound into optically pure isomers.

β-2-thienyl-alanine is a chiral compound having asymmetric carbon (chiral center) as represented by Chemical Formula 4 below.

[Chemical Formula 4]

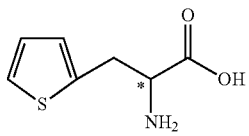

β-2-thienyl-L-alanine is an ingredient that is essentially used in the production of medicaments such as icatibant for the treatment of hereditary angioedema and labradimil for increasing the permeability of the blood-brain barrier.

The preparation of optically active β-2-thienyl-alanine using a chiral hydrogenation catalyst (Tetrahedron Asymmetry, 4, 1833(1993)) has been disclosed in the conventional art, but is problematic because an expensive chiral hydrogenation catalyst and high-pressure hydrogen gas have to be used.

Also, the preparation of β-2-thienyl-alanine through a biological reaction using microorganisms or enzymes is known. For example, preparation through an amination reaction of 2-hydroxy-3-thienyl acrylic acid (Tetrahedron Asymmetry, 8, 527(1997) and U.S. Pat. No. 5,688,672 (1997)), preparation through an amination reaction of 3-thienyl acrylic acid (Chemistry—A European Journal, 12, 2739 (2006)), and preparation through another amination reaction (The Journal of Organic Chemistry, 74, 6953 (2009)) are known. However, these methods are disadvantageous because of using enzymes or microorganisms that are difficult to handle upon mass production, and thus industrial applications thereof are limited.

PATENT LITERATURE

U.S. Pat. No. 5,688,672

NON-PATENT LITERATURE

Tetrahedron Asymmetry, 4, 1833(1993)
Tetrahedron Asymmetry, 8, 527(1997)
Chemistry—A European Journal, 12, 2739 (2006)
The Journal of Organic Chemistry, 74, 6953 (2009)

DISCLOSURE

Technical Problem

Accordingly, the present invention has been made keeping in mind the problems encountered in the related art, and the present invention is intended to provide a method of preparing a β-2-thienyl-L-alanine or β-2-thienyl-D-alanine optical isomer having high optical purity using chiral dibenzoyl tartaric acid or a derivative thereof as an optical resolving agent.

Technical Solution

Therefore, the present invention provides a method of preparing optically active β-2-thienyl-L-alanine or optically active β-2-thienyl-D-alanine, comprising reacting β-2-thienyl-DL-alanine with, as an optical resolving agent, a compound represented by Chemical Formula 1 below.

[Chemical Formula 1]

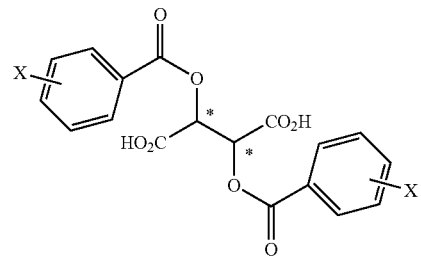

In Chemical Formula 1, X is hydrogen, a C1-C3 alkyl group, a halogen such as fluorine (F), chlorine (Cl), bromine (Br) or iodine (I), a cyano group, or a nitro group, and * represents a chiral carbon.

In addition, the present invention provides a salt of β-2-thienyl-L-alanine and compound represented by Chemical Formula 2 below.

[Chemical Formula 2]

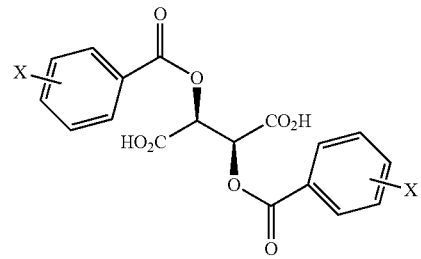

In Chemical Formula 2, X is hydrogen, a C1-C3 alkyl group, a halogen such as fluorine (F), chlorine (Cl), bromine (Br) or iodine (I), a cyano group, or a nitro group.

In addition, the present invention provides a salt of β-2-thienyl-D-alanine and compound represented by Chemical Formula 3 below.

[Chemical Formula 3]

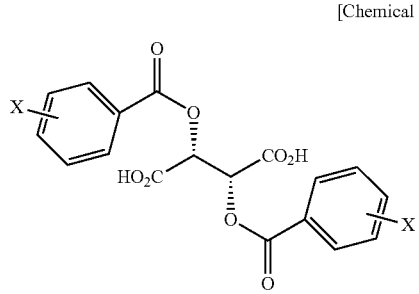

In Chemical Formula 3, X is hydrogen, a C1-C3 alkyl group, a halogen such as fluorine (F), chlorine (Cl), bromine (Br) or iodine (I), a cyano group, or a nitro group.

Advantageous Effects

According to the present invention, the method of preparing a β-2-thienyl-L-alanine or β-2-thienyl-D-alanine optical isomer enables the preparation of a β-2-thienyl-alanine optical isomer having excellent optical activity and high optical purity. Also, the method of the invention is easily applicable, generates economic benefits due to the use of an inexpensive reaction material, and enables mass production to thus realize industrial applicability.

BEST MODE

Figure 1:
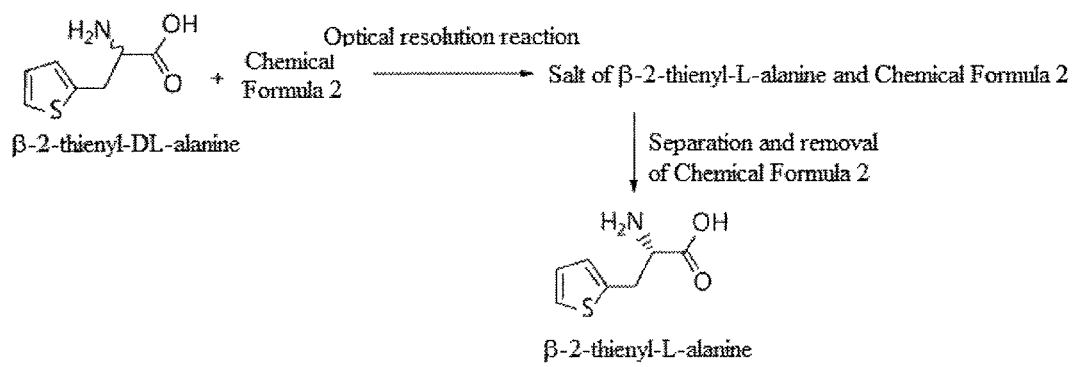
FIG. 1 schematically shows the process of preparing β-2-thienyl-L-alanine according to an embodiment of the present invention.
Figure 2:
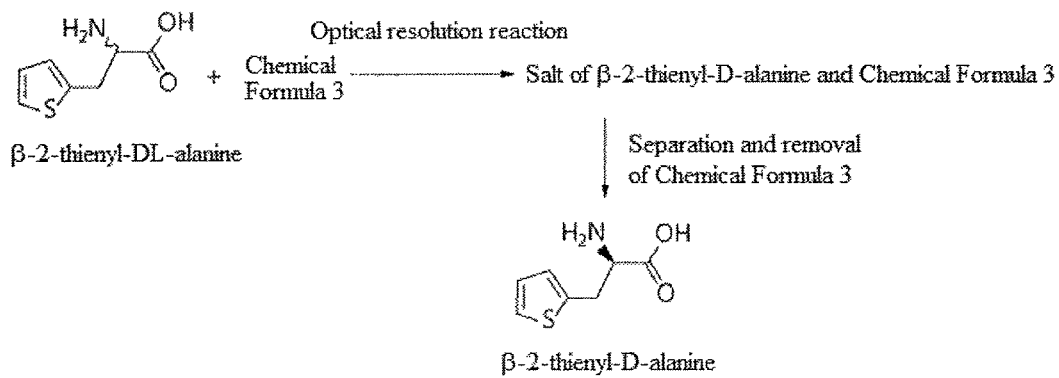
FIG. 2 schematically shows the process of preparing β-2-thienyl-D-alanine according to an embodiment of the present invention.

Generally, a process for producing an optically active compound using a chiral optical resolving agent is advantageous in that chemical processing is easily performed using a simple apparatus compared to biological processing, and is thus suitable for mass production. However, searching for and selecting chiral compounds that may be used as the optical resolving agent is regarded as very important, but is difficult.

The present inventors have identified an optical resolving agent having excellent optical resolution effects during studies on easy separation of individual isomers from the β-2-thienyl-DL-alanine isomer mixture to thus obtain β-2-thienyl-alanine optical isomers having desired optical activity and high optical purity, thus culminating in the present invention.

Hereinafter, a detailed description will be given of the present invention.

The present invention addresses a method of preparing optically active β-2-thienyl-L-alanine or optically active β-2-thienyl-D-alanine, comprising reacting β-2-thienyl-DL-alanine with, as an optical resolving agent, a compound represented by Chemical Formula 1 below.

[Chemical Formula 1]

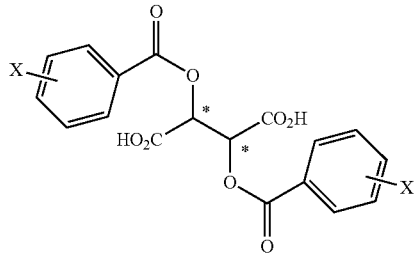

In Chemical Formula 1, X is hydrogen, a C1-C3 alkyl group, a halogen such as fluorine (F), chlorine (Cl), bromine (Br) or iodine (I), a cyano group, or a nitro group, and is preferably hydrogen, and * is a chiral carbon.

More particularly, optically active β-2-thienyl-L-alanine may be prepared by reacting β-2-thienyl-DL-alanine with, as the optical resolving agent, a compound represented by Chemical Formula 2 below.

[Chemical Formula 2]

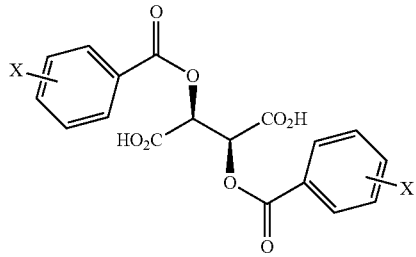

In Chemical Formula 2, X is hydrogen, a C1-C3 alkyl group, a halogen such as fluorine (F), chlorine (Cl), bromine (Br) or iodine (I), a cyano group, or a nitro group, and is preferably hydrogen.

More particularly, optically active β-2-thienyl-D-alanine may be prepared by reacting β-2-thienyl-DL-alanine with, as the optical resolving agent, a compound represented by Chemical Formula 3 below.

[Chemical Formula 3]

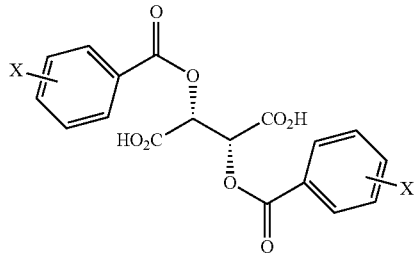

In Chemical Formula 3, X is hydrogen, a C1-C3 alkyl group, a halogen such as fluorine (F), chlorine (Cl), bromine (Br) or iodine (I), a cyano group, or a nitro group, and is preferably hydrogen.

Specifically, the present invention addresses a method of preparing β-2-thienyl-L-alanine or β-2-thienyl-D-alanine by optically resolving β-2-thienyl-DL-alanine using, as an optical resolving agent, chiral dibenzoyl tartaric acid of Chemical Formula 1 or a derivative thereof.

Below is a description of the method of preparing optically active β-2-thienyl-L-alanine by reacting β-2-thienyl-DL-alanine with, as the optical resolving agent, the compound of Chemical Formula 2 according to an embodiment of the present invention.

The preparation of optically active β-2-thienyl-L-alanine by reacting β-2-thienyl-DL-alanine with the compound of Chemical Formula 2 as the optical resolving agent is shown in Scheme 1 below.

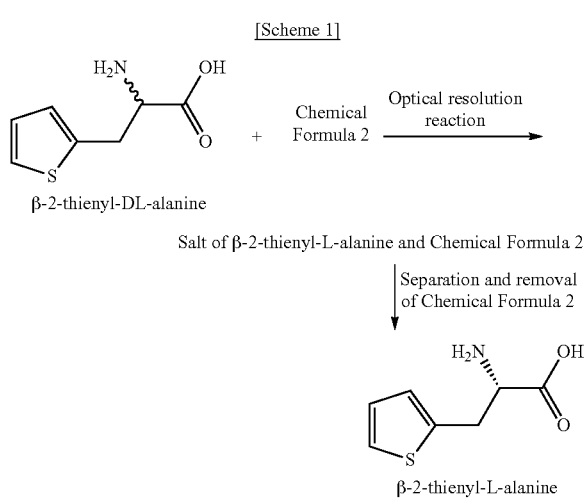

As seen in Scheme 1, the salt of β-2-thienyl-L-alanine and Chemical Formula 2 may be prepared through the optical resolution reaction of β-2-thienyl-DL-alanine and the compound of Chemical Formula 2. Here, the solvent used for the reaction may include at least one selected from among water, methanol and ethanol, and preferably water.

When the optical resolution reaction is carried out under acid conditions using an acid, such as acetic acid, hydrochloric acid, sulfuric acid or methane sulfonic acid, an optical resolution effect is preferably increased. Among the above examples of the acid, acetic acid or hydrochloric acid is preferably used.

In Scheme 1, β-2-thienyl-DL-alanine and the compound of Chemical Formula 2 are preferably reacted at an equivalent ratio of 1:0.3 to 1:1.5, and more preferably at an equivalent ratio of 1:0.4 to 1:1.2. As such, if the compound of Chemical Formula 2 is used in an amount of less than 0.3 equivalents, optical resolution efficiency decreases. On the other hand, the use thereof in an amount exceeding 1.5 equivalents is unnecessary.

Of β-2-thienyl-DL-alanine, β-2-thienyl-L-alanine is deposited in the form of a β-2-thienyl-L-alanine salt through the reaction with chiral dibenzoyl-D-tartaric acid of Chemical Formula 2 or a derivative thereof as the optical resolving agent.

The salt of β-2-thienyl-L-alanine and Chemical Formula 2 is a novel compound, and the present invention addresses a salt of β-2-thienyl-L-alanine and a compound represented by Chemical Formula 2 below.

[Chemical Formula 2]

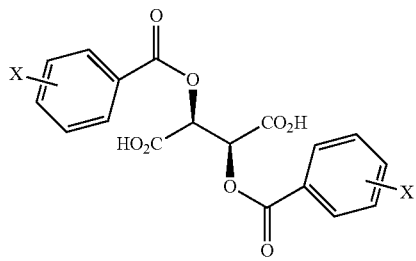

In Chemical Formula 2, X is hydrogen, a C1-C3 alkyl group, a halogen such as fluorine (F), chlorine (Cl), bromine (Br) or iodine (I), a cyano group, or a nitro group, and is preferably hydrogen.

The salt may be separated from the reaction solution through any process well-known in the art, for example, filtration, centrifugation or decantation. In particular, a filtration process may be used.

The compound of Chemical Formula 2 as the optical resolving agent is separated and removed from the salt separated from the reaction solution through filtration or the like, thereby yielding optically active β-2-thienyl-L-alanine.

The separation and removal of the optical resolving agent may be performed through a variety of typically known processes, for example, the use of an organic solvent. The salt in a solid phase obtained through optical resolution is refluxed using an organic solvent, such as acetone, methanol or ethanol, and is then cooled, whereby the optical resolving agent, namely, benzoyl-D-tartaric acid of Chemical Formula 2 or a derivative thereof, is dissolved in acetone and thus separated and removed, and β-2-thienyl-L-alanine is insoluble and thus deposited, followed by filtration, ultimately obtaining β-2-thienyl-L-alanine.

The optical purity of optically active β-2-thienyl-L-alanine thus obtained may be analyzed using a chiral column.

Also, according to the present invention, optically active β-2-thienyl-D-alanine may be prepared by reacting β-2-thienyl-DL-alanine with, as the optical resolving agent, a compound represented by Chemical Formula 3 below.

[Chemical Formula 3]

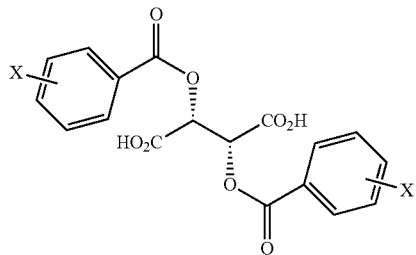

In Chemical Formula 3, X is hydrogen, a C1-C3 alkyl group, a halogen such as fluorine (F), chlorine (Cl), bromine (Br) or iodine (I), a cyano group, or a nitro group, and is preferably hydrogen.

The above reaction is shown in Scheme 2 below.

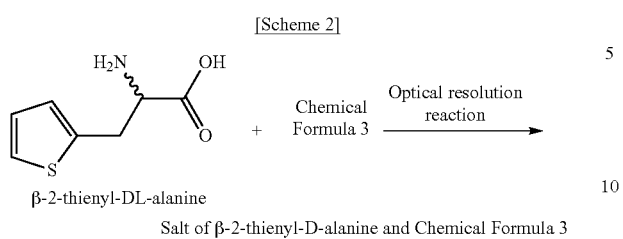

Also, the present invention addresses a salt of β-2-thienyl-D-alanine and compound represented by Chemical Formula 3 below.

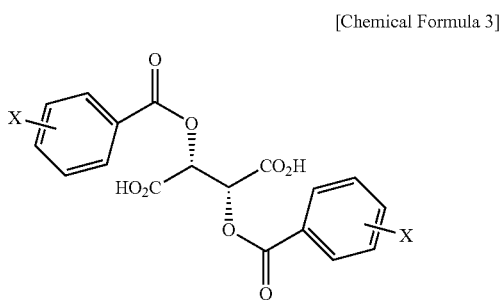

In Chemical Formula 3, X is hydrogen, a C1-C3 alkyl group, a halogen such as fluorine (F), chlorine (Cl), bromine (Br) or iodine (I), a cyano group, or a nitro group, and is preferably hydrogen.

In the present invention, β-2-thienyl-D-alanine may be prepared in the same manner as in the above preparation process of β-2-thienyl-L-alanine, with the exception that the compound of Chemical Formula 3 is used as the optical resolving agent in lieu of the compound of Chemical Formula 2.

In the present invention, β-2-thienyl-L-alanine or β-2-thienyl-D-alanine, obtained through primary optical resolution, may be further subjected to an optical resolution reaction using the compound of Chemical Formula 2 or the compound of Chemical Formula 3, thereby yielding optically active β-2-thienyl-L-alanine or optically active β-2-thienyl-D-alanine.

MODE FOR INVENTION

A better understanding of the present invention may be obtained via the following examples, which are merely set forth to illustrate but are not to be construed as limiting the scope of the present invention.

EXAMPLES

The optical purity of the salt obtained below was analyzed using a chiral column, and the analysis conditions were as follows.
Column: Chirobiotic T
Mobile phase: 80% MeOH, 20% 0.2% formic acid aqueous solution (0.2% formic acid)
Detector: UV (235 nm)

Example 1

Preparation of β-2-thienyl-L-alanine from β-2-thienyl-DL-alanine 1

200 mL of water and 50 mL of acetic acid were added with β-2-thienyl-DL-alanine (10.0 g) and dibenzoyl-D-tartaric acid (20.9 g), heated to 60° C., stirred for 1 hr, and then slowly cooled to room temperature. The resulting solution was stirred at room temperature for 1 hr, and the deposited salt of β-2-thienyl-L-alanine and dibenzoyl-D-tartaric acid was obtained through filtration (14.2 g, L/D ratio=96/4).

The obtained salt of β-2-thienyl-L-alanine and dibenzoyl-D-tartaric acid was analyzed using $^1$H-NMR. The results are as follows.

$^1$H-NMR (DMSO-$d_6$, 400 MHz): δ 3.24 (m, 2H), 3.84 (m, 1H), 5.76 (s, 2H), 6.92 (m, 2H), 7.34 (m, 1H), 7.52 (m, 4H), 7.66 (m, 2H), 7.97 (m, 4H)

The salt thus obtained was added with 210 mL of acetone, refluxed for 2 hr, and then cooled to room temperature, after which the deposited β-2-thienyl-L-alanine was obtained (4.3 g, L/D ratio=96/4).

The obtained β-2-thienyl-L-alanine was analyzed using $^1$H-NMR. The results are as follows.

$^1$H-NMR (D$_2$O, 400 MHz): δ 2.99 (m, 2H), 3.33 (m, 1H), 6.76 (m, 1H), 6.85 (m, 1H), 7.13 (m, 1H)

Example 2

Preparation of β-2-thienyl-L-alanine from β-2-thienyl-DL-alanine 2

300 mL of water was added with β-2-thienyl-DL-alanine (12.0 g) and dibenzoyl-D-tartaric acid (12.6 g), further added with 37% hydrochloric acid (3 mL), heated to 70° C., stirred for 1 hr, and then slowly cooled to room temperature. The resulting solution was stirred at room temperature for 1 hr, and the deposited salt of β-2-thienyl-L-alanine and dibenzoyl-D-tartaric acid was obtained through filtration (15.6 g, L/D ratio=95/5).

The salt thus obtained was added with 250 mL of acetone, refluxed for 3 hr, and then cooled to room temperature, after which the deposited β-2-thienyl-L-alanine was obtained (L/D ratio=95/5).

Example 3

Preparation of β-2-thienyl-L-alanine from β-2-thienyl-DL-alanine 3

460 mL of water was added with β-2-thienyl-DL-alanine (18.0 g) and dibenzoyl-D-tartaric acid (19.0 g), further added with methane sulfonic acid (5.1 g), heated to 75° C., stirred for 1 hr, and then slowly cooled to room temperature. The resulting solution was stirred at room temperature for 1 hr, and the deposited salt of β-2-thienyl-L-alanine and dibenzoyl-D-tartaric acid was obtained through filtration (21.7 g, L/D ratio=94/6).

The salt thus obtained was added with 310 mL of isopropanol and 35 mL of water, refluxed for 4 hr, and then cooled to room temperature, after which the deposited β-2-thienyl-L-alanine was obtained (L/D ratio=94/6).

Example 4

Preparation of β-2-thienyl-L-alanine from β-2-thienyl-DL-alanine 4

400 mL of water and 160 mL of methanol were added with β-2-thienyl-DL-alanine (20.0 g) and di-p-toluoyl-D-tartaric acid (18.1 g), further added with 37% hydrochloric acid (6 mL), heated to 65° C., stirred for 1 hr, and then slowly cooled to room temperature. The resulting solution was stirred at room temperature for 1 hr, and the deposited salt of β-2-thienyl-L-alanine and di-p-toluoyl-D-tartaric acid was obtained through filtration (21.2 g, L/D ratio=80/20).

The obtained salt of β-2-thienyl-L-alanine and di-p-toluoyl-D-tartaric acid was analyzed using $^1$H-NMR. The results are as follows.

$^1$H-NMR (DMSO-$d_6$, 400 MHz): δ 2.36 (S, 6H), 3.23 (m, 2H), 3.80 (m, 1H), 5.71 (s, 2H), 6.94 (m, 2H), 7.35 (m, 5H), 7.84 (m, 4H)

The salt thus obtained was added with 400 mL of acetone, refluxed for 3 hr, and then cooled to room temperature, after which the deposited β-2-thienyl-L-alanine was obtained (L/D ratio=82/18).

Example 5

Preparation of β-2-thienyl-D-alanine from β-2-thienyl-DL-alanine 5

400 mL of water and 90 mL of acetic acid were added with β-2-thienyl-DL-alanine. (20.0 g) and dibenzoyl-L-tartaric acid (42 g), heated to 65° C., stirred for 1.5 hr, and then slowly cooled to room temperature. The resulting solution was stirred at room temperature for 1 hr, and the deposited salt of β-2-thienyl-D-alanine and dibenzoyl-L-tartaric acid was obtained through filtration (28.3 g, L/D ratio=4/96).

The obtained salt of β-2-thienyl-D-alanine and dibenzoyl-L-tartaric acid was analyzed using $^1$H-NMR. The results are as follows.

$^1$H-NMR (MeOH-$d_4$, 400 MHz): δ 3.43 (m, 2H), 3.93 (m, 1H), 5.95 (s, 2H), 6.97 (m, 2H), 7.31 (m, 1H), 7.49 (m, 4H), 7.63 (m, 2H), 8.11 (m, 4H)

The salt thus obtained was added with 550 mL of acetone, refluxed for 4 hr, and then cooled to room temperature, after which the deposited β-2-thienyl-D-alanine was obtained (L/D ratio=4/96).

The invention claimed is:

1. A method of preparing optically active β-2-thienyl-L-alanine, the optical purity of which is 94% or more, which comprises reacting β-2-thienyl-DL-alanine with an optical resolving agent in water, methanol, ethanol, isopropanol, acetone, or a mixture of any two or more of the foregoing under acidic conditions obtained by adding acetic acid, hydrochloric acid or methane sulfonic acid, wherein the optical resolving agent is represented by Chemical Formula 2 below, Chemical Formula 2

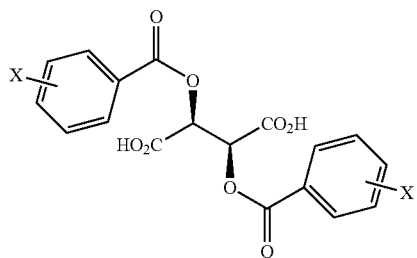

wherein X is hydrogen.

2. The method of claim 1, wherein the β-2-thienyl-DL-alanine and the compound represented by Chemical Formula 2 are reacted at an equivalent ratio of 1:0.4 to 1:1.2.

3. The method of claim 1, wherein the acidic conditions are obtained by adding acetic acid or hydrochloric acid.

4. A method of preparing optically active β-2-thienyl-D-alanine, the optical purity of which is 96% or more, which comprises reacting β-2-thienyl-DL-alanine with an optical resolving agent in water, methanol, ethanol, isopropanol, acetone, or a mixture of any two or more of the foregoing under acidic conditions obtained by adding acetic acid, hydrochloric acid or methane sulfonic acid, wherein the optical resolving agent is represented by Chemical Formula 3 below, Chemical Formula 3

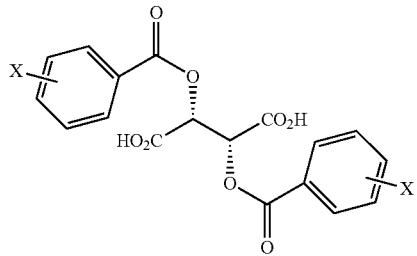

wherein X is hydrogen.

5. The method of claim 3, wherein the β-2-thienyl-DL-alanine and the compound represented by Chemical Formula 3 are reacted at an equivalent ratio of 1:0.4 to 1:1.2.

6. The method of claim 3, wherein the acidic conditions are obtained by adding acetic acid or hydrochloric acid.

* * * * *